US00PP16856P2

(12) United States Plant Patent
Smith

(10) Patent No.: US PP16,856 P2
(45) Date of Patent: Jul. 25, 2006

(54) ***CHRYSANTHEMUM* PLANT NAMED 'SUNNY YOTASHA'**

(50) Latin Name: *Chrysanthemum×morifolium*
Varietal Denomination: Sunny Yotasha

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 276 days.

(21) Appl. No.: 10/937,761

(22) Filed: Sep. 8, 2004

(51) Int. Cl.
*A01H 5/00* (2006.01)

(52) U.S. Cl. ..... Plt./295

(58) Field of Classification Search ..... Plt./295
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Sunny Yotasha', characterized by its upright, outwardly spreading and rounded plant habit; freely branching habit; dense and full appearance; uniform and freely flowering habit; small daisy-type inflorescences with elongated oblong-shaped ray florets; rich yellow-colored ray florets and darker yellow-colored disc florets; natural season flowering in mid-October in the Northern Hemisphere; and good garden performance.

2 Drawing Sheets

Botanical classification/cultivar designation: *Chrysanthemum×morifolium* cultivar Sunny Yotasha.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Sunny Yotasha'.

The new *Chrysanthemum* is a naturally-occurring whole plant mutation of the *Chrysanthemum×morifolium* cultivar Yotasha, disclosed in a U.S. Plant patent application Ser. No. 10/937,759. The new *Chrysanthemum* was discovered and selected by the Inventor as a single flowering plant within a population of plants of the cultivar Yotasha in a controlled environment in Alva, Fla. in April, 2002. The selection of this plant was based on its desirable inflorescence form, attractive floret coloration and good garden performance.

Asexual reproduction of the new cultivar by terminal vegetative cuttings in a controlled environment in Alva, Fla. since June, 2002, has shown that the unique features of this new *Chrysanthemum* are stable and reproduced true to type in successive generations.

SUMMARY OF THE INVENTION

The cultivar Sunny Yotasha has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunny Yotasha'. These characteristics in combination distinguish 'Sunny Yotasha' as a new and distinct cultivar of *Chrysanthemum:*

1. Upright, outwardly spreading and rounded plant habit.
2. Freely branching habit; dense and full plants.

3. Uniform and freely flowering habit.
4. Small daisy-type inflorescences with elongated oblong-shaped ray florets.
5. Rich yellow-colored ray florets and darker yellow-colored disc florets.
6. Natural season flowering in mid-October in the Northern Hemisphere.
7. Good garden performance.

In side-by-side comparisons conducted in Alva, Fla. under natural season conditions, plants of the new *Chrysanthemum* differed from plants of the parent, the cultivar Yotasha, in the following characteristics:

1. Plants of the new *Chrysanthemum* flowered about two or three days earlier than plants of the cultivar Yotasha.
2. Plants of the new *Chrysanthemum* and the cultivar Yotasha differed in ray floret coloration as plants of the cultivar Yotasha had bronze-colored ray florets.

Plants of the new *Chrysanthemum* can be compared to plants of the *Chrysanthemum* cultivar Julia, disclosed in U.S. Plant Pat. No. 9,020. In side-by-side comparisons conducted in Alva, Fla. under natural season conditions, plants of the new *Chrysanthemum* differed from plants of the cultivar Julia in the following characteristics:

1. Plants of the new *Chrysanthemum* were more compact and more rounded than plants of the cultivar Julia.
2. Inflorescences of plants of the new *Chrysanthemum* had fewer ray florets than inflorescences of plants of the cultivar Julia.
3. Plants of the new *Chrysanthemum* flowered about ten days later than plants of the cultivar Julia.

Plants of the new *Chrysanthemum* can also be compared to plants of the *Chrysanthemum* cultivar Gedi One Ylsap, disclosed in U.S. Plant Pat. No. 13,795. In side-by-side comparisons conducted in Alva, Fla. under natural season conditions, plants of the new *Chrysanthemum* differed from plants of the cultivar Gedi One Ylsap in the following characteristics:

1. Inflorescences of plants of the new *Chrysanthemum* had fewer ray florets than inflorescences of plants of the cultivar Gedi One Ylsap.

2. Plants of the new *Chrysanthemum* flowered about two weeks earlier than plants of the cultivar Gedi One Ylsap.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Sunny Yotasha' grown in a container.

The photograph on the second sheet comprises a close-up view of typical inflorescences of the cultivar 'Sunny Yotasha'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Sunny Yotasha.

Commercial classification: Daisy-type garden *Chrysanthemum*.

Parentage: Naturally-occurring whole plant mutation of *Chrysanthemum×morifolium* cultivar Yotasha, disclosed in a U.S. Plant patent application Ser. No. 10/937,759.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous daisy-type garden *Chrysanthemum*. Inverted triangle with mounded crown; rounded plant habit. Stems initially upright, then outwardly spreading. Freely branching with lateral branches potentially developing at every node. Moderately vigorous to vigorous.

*Plant height.*—About 16 cm.

*Plant diameter.*—About 36 cm.

*Lateral branches.*—Length: About 16.5 cm. Diameter: About 4.5 mm. Internode length: About 1.3 cm. Strength: Strong. Texture: Pubescent. Color: Close to 144A occasionally overlain with close to 79A.

*Foliage description.*—Leaf arrangement: Alternate. Length: About 4 cm. Width: About 3.2 cm. Apex: Mucronate. Base: Attenuate to truncate. Margin: Palmately and deeply lobed; sinuses parallel to convergent.

*Texture, upper and lower surfaces.*—Pubescent.

*Color.*—Developing foliage, upper surface: More green than 147A. Developing foliage, lower surface: More green than 147B. Fully expanded foliage, upper surface: More green than 147A. Fully expanded foliage, lower surface: Close to 147B. Venation, upper surface: Close to 147A to 147B. Venation, lower surface: Close to 147B to 147C.

*Petiole.*—Length: About 8 mm. Diameter: About 3 mm. Texture, upper and lower surfaces: Pubescent. Color, upper and lower surfaces: Close to 146B.

Inflorescence description:

*Appearance.*—Daisy-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences slightly cupped. Uniform and freely flowering; about 22 inflorescences develop per lateral branch. Inflorescences persistent. Inflorescences not fragrant.

*Flowering response.*—Under natural season conditions, plants flower in mid-October in the Northern Hemisphere.

*Inflorescence bud (before showing color).*—Height: About 4 mm. Diameter: About 5 mm. Shape: Oblate. Color (lower surface of phyllaries): Close to 146A.

*Inflorescence size.*—Diameter: About 4.1 cm. Depth (height): About 1.4 cm. Disc diameter: About 1.1 cm. Receptacle diameter: About 5 mm. Receptacle height: About 4 mm.

*Ray florets.*—Shape: Elongated oblong. Length: About 2.1 cm. Corolla tube length: About 3 mm. Width: About 6 mm. Apex: Emarginate. Margin: Fused. Texture: Smooth, glabrous; satiny. Surface: Concave to flat. Orientation: Initially upright, then curved upright. Number of ray florets per inflorescence: About 34 in about two to three whorls. Color: When opening and fully opened, upper surface: Close to 6A. When opening and fully opened, lower surface: Close to 6D.

*Disc florets.*—Shape: Tubular; apex dentate, five-pointed. Length: About 6 mm. Width, apex: About 2 mm. Width, base: About 1 mm. Number of disc florets per inflorescence: Numerous. Color: Immature: Close to 9A. Mature: Apex: Close to 9A. Mid-section: Close to 144A. Base: Close to 155D.

*Phyllaries.*—Quantity per inflorescence: About 22. Length: About 5.5 mm. Width: About 3 mm. Shape: Deltoid. Apex: Acute. Base: Truncate, fused. Margin: Entire. Texture, upper surface: Smooth, waxy. Texture, lower surface: Pubescent. Color, upper surface: Close to 144A. Color, lower surface: Close to 146A.

*Peduncle.*—Length: First peduncle: About 3.8 cm. Fourth peduncle: About 6.8 cm. Seventh peduncle: About 10 cm. Diameter: About 2 mm. Strength: Strong. Aspect: About 45° from vertical. Texture: Pubescent. Color: Close to 144A occasionally overlain with close to 79A.

*Reproductive organs.*—Androecium: Present on disc florets only. Anther color: 9A. Pollen: Scarce. Pollen color: Close to 12A. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good garden performance and to be tolerant to rain, wind and temperatures ranging from 0 to greater than 38° C.

It is claimed:

1. A new and distinct cultivar of *Chrysanthemum* plant named 'Sunny Yotasha', as illustrated and described.

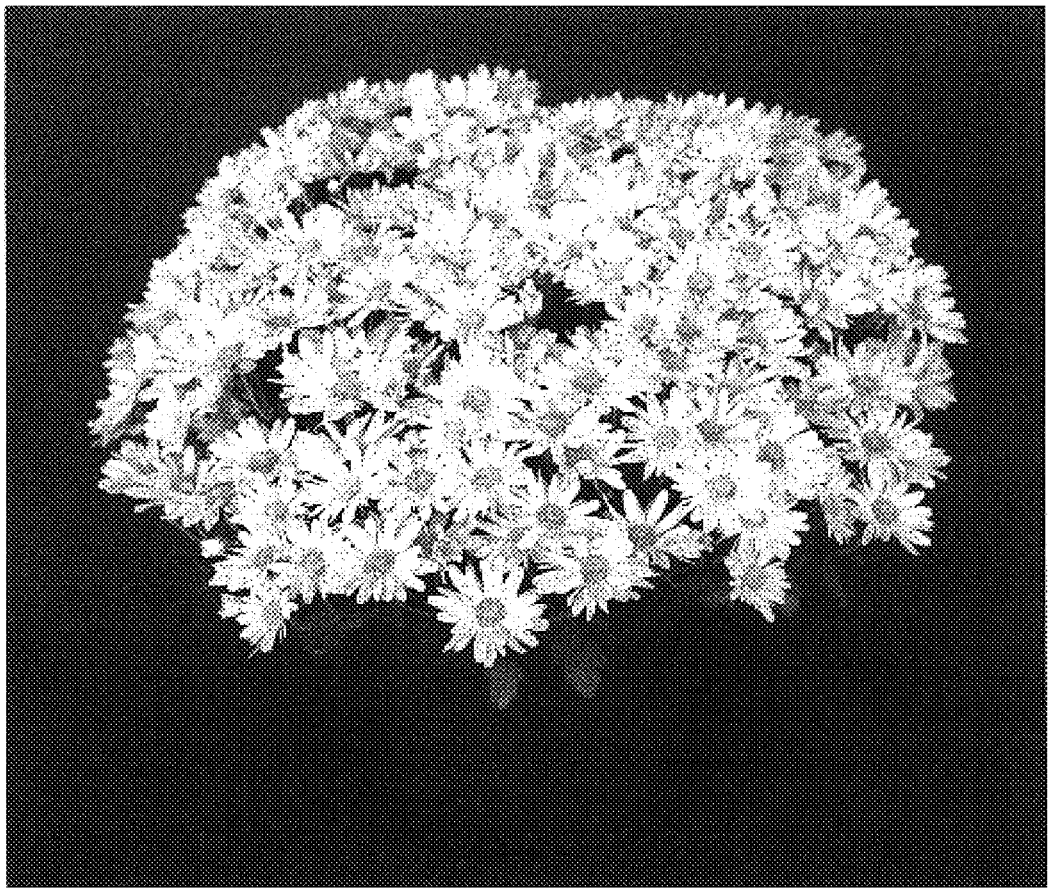

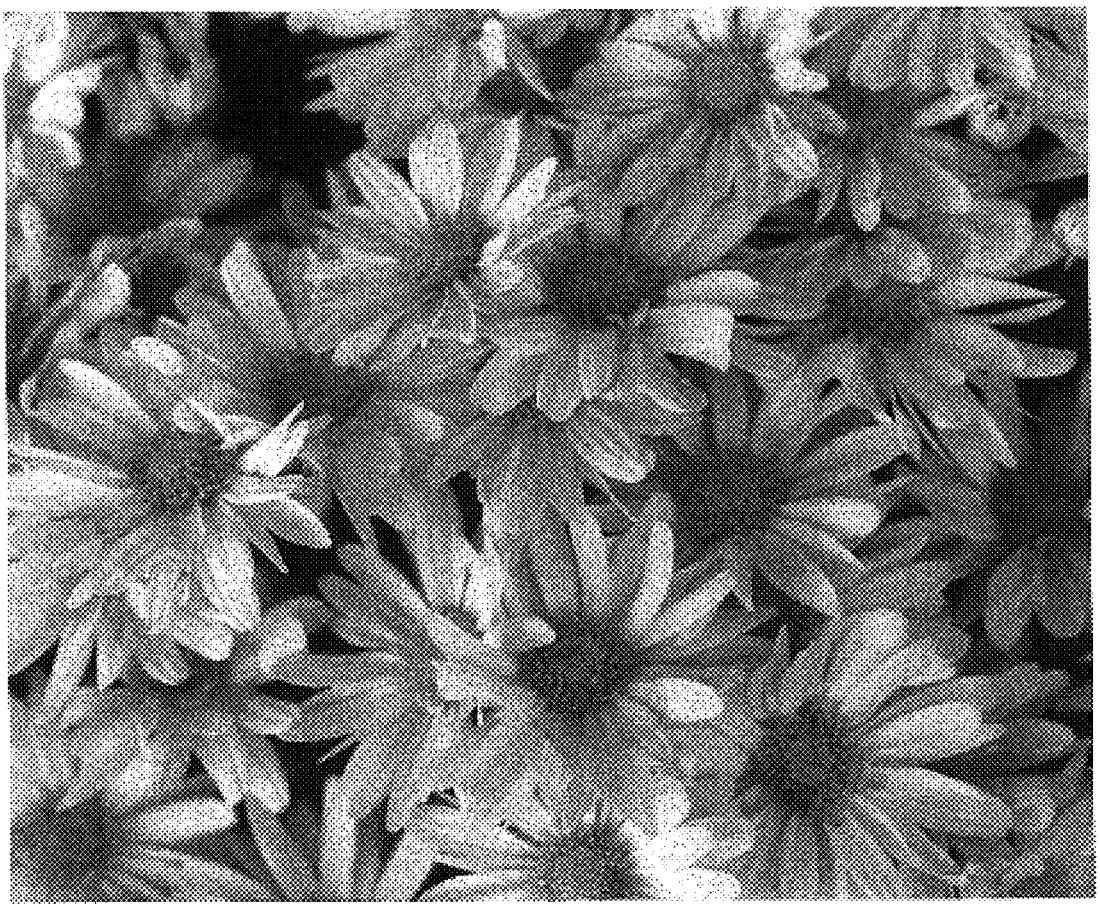

* * * * *